United States Patent
Burk et al.

(10) Patent No.: US 6,211,386 B1
(45) Date of Patent: Apr. 3, 2001

(54) PROCESS FOR ASYMMETRIC HYDROGENATION

(75) Inventors: Mark J. Burk, Landbeach; Nicholas B. Johnson, Cambridge, both of (GB); Bradley D. Hewitt, Kalamazoo, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/526,976

(22) Filed: Mar. 14, 2000

Related U.S. Application Data

(60) Provisional application No. 60/125,051, filed on Mar. 18, 1999.

(51) Int. Cl.[7] .................... C07D 309/30; C07D 309/32
(52) U.S. Cl. ...................................... 549/292; 549/294
(58) Field of Search ........................... 549/292, 294

(56) References Cited

U.S. PATENT DOCUMENTS

| | | |
|---|---|---|
| 5,171,892 | 12/1992 | Burk . |
| 5,532,395 | 7/1996 | Burk . |
| 5,559,267 | 9/1996 | Burk . |
| 5,686,631 | 11/1997 | Li et al. . |
| 6,077,963 | 6/2000 | Gage et al. . |

FOREIGN PATENT DOCUMENTS

| | | | |
|---|---|---|---|
| WO 95/30670 | 11/1995 | (WO) | C07D/309/32 |
| WO 99/12919 | 3/1999 | (WO) | C07D/309/32 |

OTHER PUBLICATIONS

J. Am. Chem. Soc., 1997, 119, 3627–3628—Asymmetric Syntheses and Absolute Stereochemistry of 5,6–Dihydro–●–pyrones, A New Class of Potent HIV Protease Inhibitors.

J. Org. Chem., 63, 7348–7356 (1998) A Convergent, Scalable Sythesis of HIV Protease Inhibitor PNY–140690.

Tetrahedron Letters, vol. 37, No. 46, pp. 8321–8324 (1996) The First Practical Asymmetric Synthesis of R and S–Warfarin.

Angew. Chem. Int. Ed. Engl. 26, (1987) 190–203; Directed Homogeneous Hydrogenation; New Synthetic Methods (65).

Angew. Chem. Int. Ed. 37, 2046—2067 (1998); Transition Metal Catalyzed Synthesis of Arylamines and Aryl Ethers from Aryl Halides and Triflates: Scope and Mechanism.

Catalytic Asymmetric Synthesis; VCH, New York, 1993, Chapter 1.

Asymmetric Catalysis in Organic Synthesis, Homogeneous Asymmetric Hydrogenation, Wiley & Sons, New York, Chapter 2, (1993).

*Primary Examiner*—Ba K. Trinh
(74) *Attorney, Agent, or Firm*—Bruce Stein

(57) ABSTRACT

The present invention is a process for the preparation of a compound of the formula:

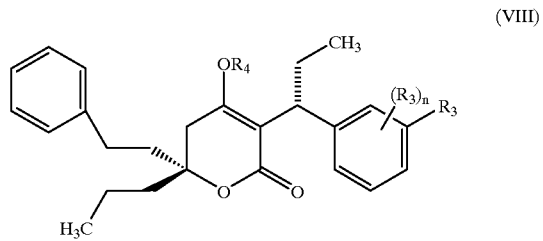

(VIII)

where $R_3$, R4 and n are defined in the specification which comprises hydrogenating a compound of the formula:

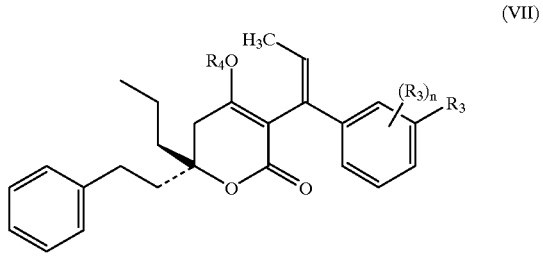

(VII)

the E-geometrical isomer thereof or a mixture of the Z- and E-isomers in the presence of catalyst containing Rh, a chiral ligand with at least one phosphorous atom where the hydrogenation is conducted in the presence of a base.

50 Claims, No Drawings

PROCESS FOR ASYMMETRIC HYDROGENATION

CROSS REFERENCE TO RELATED APPLICATIONS

This application claims the benefit of U.S. Ser. No. 60/125,051, filed Mar. 18, 1999, under 35 USC 119(e)(i).

BACKGROUND OF THE INVENTION

1. Field of the Invention

The present invention is an improved process for the asymmetric hydrogenation of a double bond.

2. Description of the Related Art

[R-(R*,R*)]-N-[3-[1-[5,6-dihydro-4-hydroxy-2-oxo-6-(2-phenylethyl)-6-propyl-2H-pyran-3-yl]propyl]phenyl]-5-(trifluoromethyl)-2-pyridinesulfonamide is a protease inhibitor useful in treating humans infected with the HIV virus (AIDS) and is known as tipranavir.

J. Am. Chem. Soc., 119, 3627 (1997) and the J. Org. Chem., 63, 7348 (1998) both disclose processes to produce tipranavir.

U.S. patent application Ser. No. 09/213,887 discloses a process to convert the ketone (I) to the cyclic ester (VI) as set forth in CHART A and EXAMPLES 1 thru 4 of U.S. patent application Ser. No. 09/213,887. CHART F of U.S. patent application Ser. No. 09/213,887 then discloses the transformation of the cyclic ester (VI) to the corresponding 6(R)- and 6(S)-olefin (XXV) by the process of EXAMPLE 16 which is then hydrogenated by the process of EXAMPLE 17 to produce the nitro-α,β-unsaturated ester (XVII). The nitro-α,β-unsaturated ester (XVII) is then transformed into tipranavir (XIX) by the process of EXAMPLES 14 and 15.

Hydrogenation reactions are very well known to those skilled in the art. In some hydrogenation reactions the product produced has an asymmetric carbon atom as in EXAMPLE 17 of U.S. patent application Ser. No. 09/213,887. It is known to those skilled in the art that the enantioselectivity of the hydrogenation can be influenced by the catalyst used. U.S. Pat. Nos. 5,171,892, 5,532,395 and 5,559,267 disclose enantioselective rhodium catalysts known as "DuPHOS" catalysts which can provide enantioselective hydrogenations in the 70 to 89% range.

U.S. Pat. No. 5,686,631 and Tetrahedron Lett. 37, 8321 (1996) disclose an asymmetric hydrogenation of warfarin, a 2-pyranone derivative, with 89% enantioselectivity with a DuPHOS catalyst. However, warfarin has a phenyl ring attached to the 5,6-position of the compounds of the present invention which would change the three dimensional nature of the compound. Chem. Rev. 93, 1307 (1993) and Chem. Int. Ed. Engl. 26, 190 (1987) disclose that an important feature in some stereoselective hydrogenation reactions is a secondary coordination of functional groups.

Catalytic Asymmetric Synthesis; VCH, New York, 1993, Chapter 1 and Asymmetric Catalysis in Organic Synthesis, Wiley & Sons, New York, 1993, Chapter 2 disclose an important feature of stereoselective hydrogenation of olefin substrates is the geometry (E or Z) of the double bond. It is known that one isomer of an olefin would be a preferred substrate to obtain higher enantioselectivity of a particular enantiomeric product.

SUMMARY OF INVENTION

Disclosed is a process for the preparation of a compound of the formula:

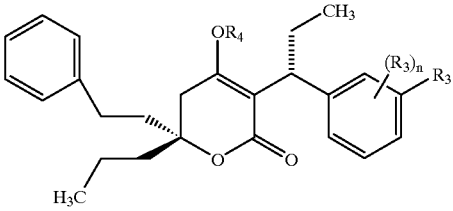

(VIII)

where $R_3$ is selected from the group consisting of:
—$NO_2$,
—$NH_2$,
—NH—$SO_2$-[4-trifluoromethylpyridin-2-yl],
—N(—$CH_2$-φ)$_2$,
—N($R_{3-1}$)($R_{3-2}$) where $R_{3-1}$ and $R_{3-2}$ are the same or different and are:
—H,
—CO—O—(t-butyl),
—CO—O—$CH_2$-φ,
—CO—$CH_3$,
—CO-φ,
—Cl,
—Br,
—I,
—OH,
—O—$SO_2$—$CF_3$, where n is 0 or 1 with the provisos, (1) that when n is 0 the $R_3$ group must be in the meta position and (2) that when n is 1, one of $R_3$ must be —Cl, —Br, —I, —OH or —O—$SO_2$—$CF_3$, where $R_4$ is selected from the group consisting of —H and —Si($CH_3$)$_3$, which comprises hydrogenating a compound of the formula:

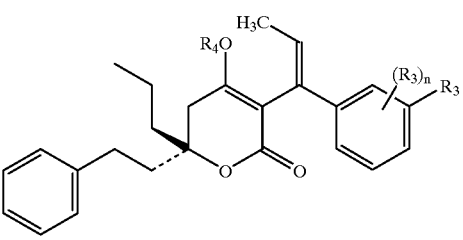

(VII)

the E-geometrical isomer thereof or a mixture of the Z- and E-isomers, where $R_3$ and $R_4$ are as defined above, in the presence of catalyst containing Rh, a chiral ligand with at least one phosphorous atom where the hydrogenation is conducted in the presence of a base.

Also disclosed is a process for the preparation of a compound of the formula:

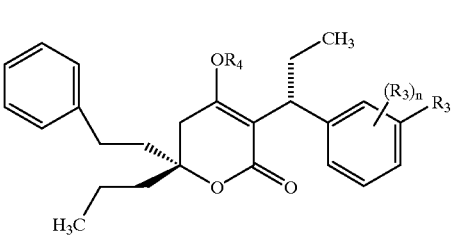

(VIII)

where $R_3$ and n are as defined above, where $R_4$ is selected from the group consisting of Na$^+$, K$^+$, Li$^+$, Cs$^+$ and $(R_{4-1})_4N^+$ where $R_{4-1}$ are the same or different and are $CH_3$—, $C_2H_5$—, $C_4H_9$—, $\phi$-$CH_2$— and $C_8H_{17}$— which comprises hydrogenating a compound of the formula:

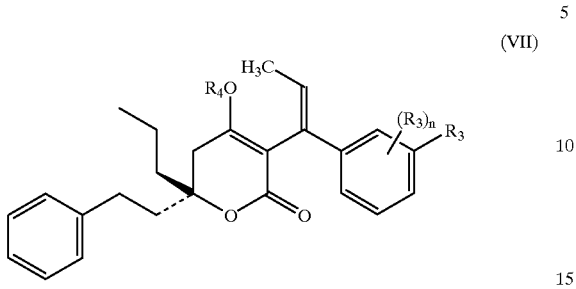

(VII)

the E-geometrical isomer thereof or a mixture of the Z- and E-isomers in the presence of catalyst containing Rh, a chiral ligand with at least one phosphorous atom. Additionally disclosed is a process for the preparation of a compound of the formula

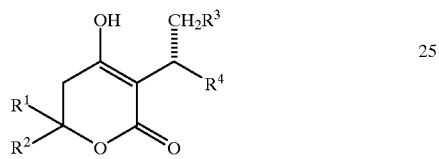

where $R^1$ and $R^2$ are the same or different groups and are each —H or up to 30 carbon atoms;

where $R^3$ is $C_1$–$C_8$ alkyl;

where $R^4$ is aryl optionally substituted by a functional group; and where $R_4$ is —H or —$Si(CH_3)_3$ which comprises asymmetric hydrogenation of a compound of the formula

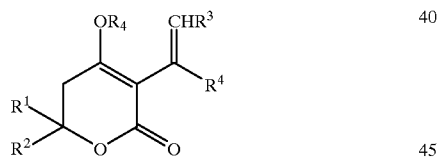

where $R^1$, $R^2$, $R^3$, $R^4$ and $R_4$ is as defined above in the presence of as a catalyst a complex of a transition metal and a chiral phosphine ligand with the proviso that when one of $R^1$ or $R^2$ is propyl, the other of $R^1$ or $R^2$ is not 1-(2-phenyl)ethyl.

DETAILED DESCRIPTION OF THE INVENTION

The present invention is an improved catalytic hydrogenation of the olefin (VII) to the corresponding chiral compound (VIII); the improvement is the addition of base or starting with the enolate. Another invention is the improved catalytic hydrogenation of the olefin where when one of $R^1$ or $R^2$ is propyl the other of $R^1$ or $R^2$ is not 1-(2-phenyl)ethyl.

It is preferred that the catalyst be the (2R,5R)-enantiomer of a catalyst of the formula:

$X_1$—$Rh^+$-cyclooctadiene $X_2^-$ where $X_1$ is selected from the group consisting of:
(1) BPE

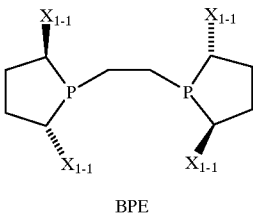

BPE where $X_{1-1}$ is —$CH_3$ or —$C_2H_5$,
(2) DuPHOS

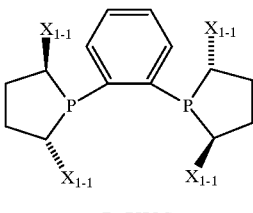

DuPHOS where $X_{1-1}$ is as defined above;
where $X_2$ is selected from the group consisting of:
(1) $BF_4^-$ and
(2) $CF_3$—CO—$O^-$.

It is preferred that the olefin used be a mixture of E/Z-isomers of (VII). It is preferred that n be 0. For the olefin (VII), $R_3$ is selected from the group consisting of:
—$NO_2$,
—$NH_2$,
—NH—$SO_2$-[4-trifluoromethylpyridin-2-yl],
—N(—$CH_2$-$\phi$)$_2$,
—N($R_{3-1}$)($R_{3-2}$) where $R_{3-1}$ and $R_{3-2}$ are the same or different and are:
—H,
—CO—O—(t-butyl),
—CO—O—$CH_2$-$\phi$,
—CO—$CH_3$,
—CO-$\phi$,
—Cl,
—Br,
—I
—OH,
—O—$SO_2$—$CF_3$; it is preferred that $R_3$ is —$NO_2$, —$NH_2$ and —N($R_{3-1}$)($R_{3-2}$) where one of $R_{3-1}$ and $R_{3-2}$ is —H and the other is —CO—O—(t-butyl); it is more preferred that $R_3$ is —$NO_2$. n is 0 or 1 with the provisos, (1) that when n is 0 the $R_3$ group must be in the meta position and (2) that when n is 1, one of $R_3$ must be —Cl, —Br, —I, —OH or —O—$SO_2$—$CF_3$. When n is 0, the chiral compound (VIII) is represented with one $R_3$ group as (VIII-A) and when n is 1, the chiral compound (VIII) is represented with two $R_3$ groups as (VIII-B). $R_4$ is selected from the group consisting of —H, —$Si(CH_3)_3$, $Na^+$, $K^+$, $Li^+$, $Cs^+$ and $(R_{4-1})_4N^+$ where $R_{4-1}$ are the same or different and are $CH_3$—, $C_2H_5$—, $C_4H_9$—, $\phi$-$CH_2$— and $C_8H_{17}$—. It is preferred that the compound (VIII) is [3α(R),6(R)]5,6-dihydro-4-hydroxy-3-[1-(3-nitrophenyl)propyl]-6-[1-(2-phenyl)ethyl]-6-propyl-2H-pyran-2-one.

The process of the present invention has two very similar forms. In the first form of the process, the olefin (VII) has at the 4-position the hydroxy functionality or a silylated ether derivative; $R_4$ is either —H or —Si(CH$_3$)$_3$. The alternative form starts with the enolate at C-4, where $R_4$ is a cation, Na$^+$, K$^+$, Li$^+$, Cs$^+$, $(R_{4-1})_4$N$^+$ where the $R_{4-1}$ are the same or different and are CH$_3$—, C$_2$H$_5$—, C$_4$H$_9$—, $\phi$-CH$_2$— and C$_8$H$_{17}$—.

When $R_4$ is either —H or —Si(CH$_3$)$_3$ the reaction requires a base. The operable bases are those where the base has a pK$_a$>5; it is preferred that the base be selected from the group consisting of hydroxide, alkoxide where the alkyl group is from C$_1$–C$_5$, bicarbonate, carbonate, di- and tribasic phosphate, borate, fluoride and R$_a$R$_b$R$_c$N where R$_a$, R$_b$ and R$_c$ are the same or different and are:

H—,

C$_1$–C$_4$ alkyl, $\phi$-,

R$_d$R$_e$R$_f$Si— where the R$_d$, R$_e$ and R$_f$ are the same or different and are C$_1$–C$_3$ alkyl with the proviso that not more than one of the R$_a$, R$_b$ and R$_c$ are H—; it is more preferred that the base be selected from the group consisting of hydroxide, methoxide, ethoxide, t-butoxide, t-amylate, s-butoxide, di- and tribasic phosphate and carbonate; it is even more preferred that the base be is methoxide or carbonate. The amount of base required is in an amount of less than one equivalent; it is preferred that the base be present in an amount of about 0.1 equivalents.

It is preferred that the catalyst containing Rh, a chiral ligand with at least one phosphorous atom, be a catalyst of the formula:

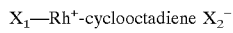

where $X_1$ is selected from the group consisting of:

(1) BPE

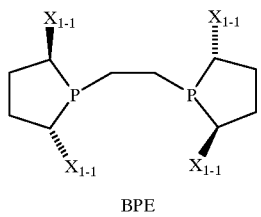

BPE where $X_{1-1}$ is —CH$_3$ or —C$_2$H$_5$, and (2) DuPHOS

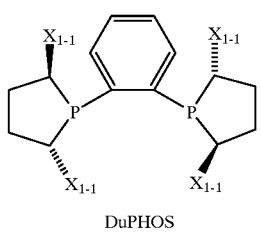

DuPHOS where $X_{1-1}$ is as defined above; where $X_2$ is selected from the group consisting of BF$_4^-$ and CF$_3$—CO—O$^-$. These catalysts are well known to those skilled in the art, see for example U.S. Pat. Nos. 5,171,892, 5,532, 395 and 5,559,267. For the catalyst it is preferred that $X_1$ be of formula (2). It is also preferred that $X_2$ be BF$_4^-$ and $X_{1-1}$ be —CH$_3$. The amount of catalyst is expressed as a ratio (in moles) of substrate/catalyst. Operable ratios include where the ratio (in moles) of substrate/catalyst is from about 200/1 to 5,000/1; it is preferred that the ratio (in moles) of substrate/catalyst is from about 500/1 to 3,000/1; it is more preferred that the ratio (in moles) of substrate/catalyst is from about 1,000/1 to 2,000/1.

The process of the invention is performed in a temperature range of about 20° to about 120°; preferably in a temperature range of from about 40° to about 80°; more preferably in a temperature range of from about 50° to about 65°.

The process of the invention is performed under a pressure in the range of about from about 40 to about 1,000 psi; preferably in a range of about 70 to about 1,000 psi; more preferably in a range of from about 70 to about 90 psi Alternatively the pressure can be expressed as kPa which is kiloPascals of hydrogen.

The solvent(s) utilized in the present invention are those well known to those skilled in the art for performing hydrogenation reactions and are not critical as long a the olefin (VII) is in solution. It is preferred that the solvent be methanol, ethanol, acetone, methylene chloride, ethyl acetate, acetonitrile, toluene. It is more preferred that the solvent be methanol or toluene.

When performing the process of the present invention, it is preferred to combine the olefin (VII), the base, solvent and hydrogen before adding the catalyst. It is even more preferred to combine all these reagents and bring the reaction mixture to reaction temperature prior to adding the catalyst.

For commercial reasons, the process of the present invention should be complete in less than 72 hours. Preferably the process is complete in about 24 to about 48 hours and have a selectivity of diastereomeric excess of about 80%, preferably a diastereomeric excess of greater than about 90%. It is realized that not all reactions conditions set for above will produce the desired results if the minimum of each range is selected. However, one skilled in the art is well aware of this and can select the optimum pressure to be used with the minimum temperature or the optimum temperature to be used with the minimum pressure, etc. It is preferred that when the temperature is about 20°, the pressure is at least about 150 psi or greater to complete the reaction in about 72 hr. If the temperature is about 20° and it is desired to complete the reaction in about 48 hr, about 200 psi is required. Likewise when the pressure is 40 psi, it is preferred that the temperature is 48° or greater to complete the reaction in 72 hr. If it is desired to complete the reaction in 48 hr, at least 58° is necessary.

The chiral compound (VIII-A or VIII-B) can be either isolated or carried on in situ. It is preferred that the chiral compound (VIII-A or VIII-B) be isolated in order to determine the diastereomeric purity of the product.

When $R_4$ is selected from the group consisting of Na$^+$, K$^+$, Li$^+$, Cs$^+$ and $(R_{4-1})_4$N$^+$ then the hydrogenation process does not require that any base be added.

When n is 0, $R_3$ must be in the meta position. The reason is in tipranavir the substitutent on the phenyl ring is in the meta position. CHART B discloses the preferred process when n is 0. It is preferred that $R_3$ be —NO$_2$. Asymmetric hydrogenation of the olefin (VII) produces the chiral compound (VIII-A). When $R_3$ is —NO$_2$, it is next reduced (EXAMPLE 7) to the amino intermediate (IX) followed by formation of the sulfonamide tipranavir product (X) by the process of EXAMPLE 8. If $R_3$ is —NH$_2$, then the asymmetric hydrogenation of the olefin (VII) produces the amino intermediate (IX) directly. If $R_3$ is NH—$SO_2$-[4-trifluoromethylpyridin-2-yl], then the desired tipranavir (X) is produced directly. If $R_3$ is —N(—$CH_2$-φ)$_2$ or —N($R_{3-1}$) ($R_{3-1}$) then the benzyl or $R_{3-1}$ groups are removed as is known to those skilled in the art by hydrogenation (in the presence of a suitable supported transition metal catalyst, e.g. Pd/C) or by hydrolysis (treat with acids or bases in a suitable solvent) to cleave the benzyl or $R_{3-1}$ groups to produce compound (IX). If $R_3$ is halogen then, compound (VII-A) can not be directly converted to compound (IX). It must first be converted to a compound where the halogen group is replaced by a non-halogen $R_3$ group. The compound containing the non-halogen $R_3$ group is then transformed to compound (IX). When $R_3$ is halogen in compound (VII-A) the halogen group is transformed to a non-halogen $R_3$ group by the action of a suitable transition metal catalyst in the presence of a suitable amine, such as dibenzylamine in a manners reviewed and described in *Angew. Chem. Int. Ed.* 37, 2046 (1998) to provide the intermediate compound (XI), where $R_3$ is —N(—$CH_2$φ)$_2$ which is converted, as described previously to compound (IX). Other suitable amines include hexamethyldisilazane, producing an intermediate (XI), where $R_3$ is —N[Si($CH_3$)$_3$]$_2$, which can be hydrolyzed to provide compound (IX). If $R_3$ is —O—$SO_2$—$CF_3$ then compound (VII-A) one skilled in the art would know that this compound could converted to compound (IX) in manner similar to when $R_3$ is halogen. If $R_3$ is —OH, then one skilled in the art would first convert the —OH to —O—$SO_2$—$CF_3$ or similar sulfonate ester, and then proceed to compound (IX) in the manner described for those compounds.

CHART C discloses the invention when n is 1. When n is 1, one of the $R_3$ groups must be in the meta position. The other $R_3$ group need not be in the meta position. When n is 1, one of the $R_3$ groups must be —Cl, —Br, —I, —OH or —O—$SO_2$—$CF_3$. It is this $R_3$ group, —Cl, —Br, —I, —OH or —O—$SO_2$—$CF_3$ which does not have to be in the meta position. The nitrogen functionality of $R_3$ must be in the meta position. The second $R_3$ group can remain on during the hydrogenation of the olefin (VII) to the chiral compound (VIII) and then would be removed in a subsequent reaction leaving the chiral compound (VIII) or the amino intermediate (IX) with just the one $R_3$ group in the desired meta position.

The other process of the invention is the improved catalytic hydrogenation of the olefin where when one of $R^1$ or $R^2$ is propyl, the other of $R^1$ or $R^2$ is not 1-(2-phenyl)ethyl. This proviso is to expressly exclude the compound formula (VIII), [3α(R),6(R)]5,6-dihydro-4-hydroxy-3-[1-(3-nitrophenyl)propyl]-6-[1-(2-phenyl)ethyl]-6-propyl-2H-pyran-2-one. This process is practiced analogously. For this process it is preferred that the catalyst has for the chiral phosphine ligand the following group:

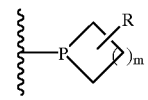

where m is 0 or an integer from 1 to 6, and R represents at least one non-hydrogen organic group of up to 30 carbon atoms. It is more preferred that the ligand is of the following formulas, where Linker and R' are independently any non-hydrogen organic group of up to 30 carbon atoms.

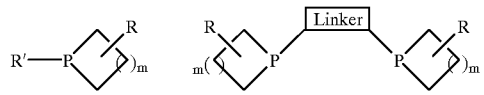

It is preferred that $R^1$ is $C_6$–$C_{15}$ arylalkyl; it is more preferred that $R^1$ is phenylethyl. It is preferred that $R^2$ is $C_1$–$C_8$ alkyl; it is more preferred that $R^2$ is n-propyl. It is preferred that $R^3$ is methyl and $R^4$ is phenyl substituted by a functional group. It is preferred that the functional group is —$NO_2$.

It is preferred that the ligand is a chiral bis-phosphine of 1,2-bis(phospholano)benzene (DuPHOS) or 1,2-bis(phospholano)ethane (BPE) of the respective formulas:

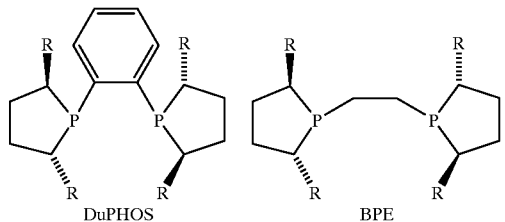

DuPHOS        BPE or the opposite enantiomer thereof, where each R is any non-hydrogen organic group. It is preferred that each R is $C_1$–$C_4$ linear or branched alkyl group. It is preferred that the transition metal is Rh, Ru or Ir; it is more preferred that the transition metal be Rh. With regard to base it is preferred that the amount of base be a catalytic quantity; it is preferred that the base is NaOMe or $Na_2CO_3$. It is preferred that the reaction temperature be 0–125° C.; more preferably 25–75° C. It is preferred that the reaction pressure is 35 to 14,000 kPa $H_2$, more preferably 350 to 1,400 kPa $H_2$ and even more preferably 500 to 700 kPa $H_2$. It is preferred the reaction is conducted in a solvent that is methanol or toluene. It is preferred that the catalyst is 0.1 mole % [((R,R)-Me-DUPHOS)Rh(COD)]$BF_4$ with 10% mole % $Na_2CO_3$ co-catalyst, the temperature is 50 to 60° C., the pressure is 500 to 700 kPa $H_2$ and the solvent is methanol. It is also preferred that the product be crystallized from aqueous methanol which enriches the diastereomeric excess of the product.

DEFINITIONS AND CONVENTIONS

The definitions and explanations below are for the terms as used throughout this entire document including both the specification and the claims.

I. Conventions for Formulas and Definitions of Variables

The chemical formulas representing various compounds or molecular fragments in the specification and claims may contain variable substituents in addition to expressly defined structural features. These variable substituents are identified by a letter or a letter followed by a numerical subscript, for example, "$Z_1$" or "$R_i$" where "i" is an integer. These variable substituents are either monovalent or bivalent, that is, they represent a group attached to the formula by one or two chemical bonds. For example, a group $Z_1$ would represent a bivalent variable if attached to the formula $CH_3$—C(=$Z_1$)H. Groups $R_i$ and $R_j$ would represent monovalent variable substituents if attached to the formula $CH_3$—$CH_2$—C($R_i$)($R_j$)—H. When chemical formulas are drawn in a linear fashion, such as those above, variable substituents contained in parentheses are bonded to the atom immediately to the left of the variable substituent enclosed in parenthesis. When two or more consecutive variable substituents are enclosed in parentheses, each of the consecutive variable substituents is bonded to the immediately preceding atom to the left which is not enclosed in parentheses. Thus, in the formula above, both $R_i$ and $R_j$ are bonded to the preceding carbon atom. Also, for any molecule with an established system of carbon atom numbering, such as steroids, these carbon atoms are designated as $C_i$, where "i" is the integer corresponding to the carbon atom number. For example, $C_6$ represents the 6 position or carbon atom number in the steroid nucleus as traditionally designated by those skilled in the art of steroid chemistry. Likewise the term "$R_6$" represents a variable substituent (either monovalent or bivalent) at the $C_6$ position.

Chemical formulas or portions thereof drawn in a linear fashion represent atoms in a linear chain. The symbol "—" in general represents a bond between two atoms in the chain. Thus $CH_3$—O—$CH_2$—$CH(R_i)$—$CH_3$ represents a 2-substituted-1-methoxypropane compound. In a similar fashion, the symbol "=" represents a double bond, e.g., $CH_2$=$C(R_i)$—O—$CH_3$, and the symbol "≡" represents a triple bond, e.g., HC≡C—$CH(R_i)$—$CH_2$—$CH_3$. Carbonyl groups are represented in either one of two ways: —CO— or —C(=O)—, with the former being preferred for simplicity.

A rigid cyclic (ring) structure for any compounds herein defines an orientation with respect to the plane of the ring for substituents attached to each carbon atom of the rigid cyclic compound. For saturated compounds which have two substituents attached to a carbon atom which is part of a cyclic system, —$C(X_1)(X_2)$— the two substituents may be in either an axial or equatorial position relative to the ring and may change between axial/equatorial. However, the position of the two substituents relative to the ring and each other remains fixed. While either substituent at times may lie in the plane of the ring (equatorial) rather than above or below the plane (axial), one substituent is always above the other. In chemical structural formulas depicting such compounds, a substituent ($X_1$) which is "below" another substituent ($X_2$) will be identified as being in the alpha (α) configuration and is identified by a broken, dashed or dotted line attachment to the carbon atom, i.e., by the symbol "- - -" or ". . .". The corresponding substituent attached "above" ($X_2$) the other ($X_1$) is identified as being in the beta (β) configuration and is indicated by an unbroken or solid line attachment to the carbon atom.

When a variable substituent is bivalent, the valences may be taken together or separately or both in the definition of the variable. For example, a variable $R_i$ attached to a carbon atom as —$C(=R_i)$— might be bivalent and be defined as oxo or keto (thus forming a carbonyl group (—CO—) or as two separately attached monovalent variable substituents a-$R_{i-j}$ and β-$R_{i-k}$. When a bivalent variable, $R_i$, is defined to consist of two monovalent variable substituents, the convention used to define the bivalent variable is of the form "a-$R_{i-j}$:β-$R_{i-k}$" or some variant thereof. In such a case both a-$R_{i-j}$ and β-$R_{i-k}$ are attached to the carbon atom to give —C(a-$R_{i-j}$)(β-$R_{i-k}$)—. For example, when the bivalent variable $R_6$, —$C(=R_6)$— is defined to consist of two monovalent variable substituents, the two monovalent variable substituents are a-$R_{6-1}$:β-$R_{6-2}$, . . . a-$R_{6-9}$:β-$R_{6-10}$, etc., giving —C(a-$R_{6-1}$)(β-$R_{6-2}$)—, . . . —C(a-$R_{6-9}$)(β-$R_{6-10}$)—, etc. Likewise, for the bivalent variable $R_{11}$, —$C(=R_{11})$—, two monovalent variable substituents are a-$R_{11-1}$:β-$R_{11-2}$. For a ring substituent for which separate a and β orientations do not exist (e.g. due to the presence of a carbon carbon double bond in the ring), and for a substituent bonded to a carbon atom which is not part of a ring the above convention is still used, but the a and β designations are omitted.

Just as a bivalent variable may be defined as two separate monovalent variable substituents, two separate monovalent variable substituents may be defined to be taken together to form a bivalent variable. For example, in the formula —$C_1(R_i)$H—$C_2(R_j)$H— ($C_1$ and $C_2$ define arbitrarily a first and second carbon atom, respectively) $R_i$ and $R_j$ may be defined to be taken together to form (1) a second bond between $C_1$ and $C_2$ or (2) a bivalent group such as oxa (—O—) and the formula thereby describes an epoxide. When $R_i$ and $R_j$ are taken together to form a more complex entity, such as the group —X—Y—, then the orientation of the entity is such that $C_1$ in the above formula is bonded to X and $C_2$ is bonded to Y. Thus, by convention the designation ". . . $R_i$ and $R_j$ are taken together to form —$CH_2$—$CH_2$—O—CO— . . ." means a lactone in which the carbonyl is bonded to $C_2$. However, when designated ". . . $R_j$ and $R_i$ are taken together to form —CO—O—$CH_2$—$CH_2$— the convention means a lactone in which the carbonyl is bonded to $C_1$.

The carbon atom content of variable substituents is indicated in one of two ways. The first method uses a prefix to the entire name of the variable such as "$C_1$–$C_4$", where both "1" and "4" are integers representing the minimum and maximum number of carbon atoms in the variable. The prefix is separated from the variable by a space. For example, "$C_1$–$C_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus $C_2$–$C_4$ alkoxycarbonyl describes a group $CH_3$—$(CH_2)_n$—O—CO—where n is zero, one or two. By the second method the carbon atom content of only each portion of the definition is indicated separately by enclosing the "$C_i$–$C_j$" designation in parentheses and placing it immediately (no intervening space) before the portion of the definition being defined. By this optional convention ($C_1$–$C_3$)alkoxycarbonyl has the same meaning as $C_2$–$C_4$ alkoxycarbonyl because the "$C_1$–$C_3$" refers only to the carbon atom content of the alkoxy group. Similarly while both $C_2$–$C_6$ alkoxyalkyl and ($C_1$–$C_3$) alkoxy($C_1$–$C_3$)alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

When the claims contain a fairly complex (cyclic) substituent, at the end of the phrase naming/designating that particular substituent will be a notation in (parentheses) which will correspond to the same name/designation in one of the CHARTS which will also set forth the chemical structural formula of that particular substituent.

II. Definitions

All temperatures are in degrees Centigrade.

TLC refers to thin-layer chromatography.

HPLC refers to high pressure liquid chromatography.

THF refers to tetrahydrofuran.

CDI refers to 1,1'-carbonyldiimidazole.

Saline refers to an aqueous saturated sodium chloride solution.

IR refers to infrared spectroscopy.

CMR refers to C-13 magnetic resonance spectroscopy, chemical shifts are reported in ppm (d) downfield from TMS.

NMR refers to nuclear (proton) magnetic resonance spectroscopy, chemical shifts are reported in ppm (d) downfield from tetramethylsilane.

-φ refers to phenyl ($C_6H_5$).

MS refers to mass spectrometry expressed as m/e, m/z or mass/charge unit. $[M+H]^+$ refers to the positive ion of a parent plus a hydrogen atom. EI refers to electron impact. CI refers to chemical ionization. FAB refers to fast atom bombardment.

When solvent pairs are used, the ratios of solvents used are volume/volume (v/v).

psi refers to pounds per $ft^2$.

kPa refers to kiloPascals of hydrogen.

The "chiral compound (VIII)" includes both the chiral compound with one $R_3$ group VIII-A) and with two $R_3$ groups (VIII-B).

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Example 1

Ethyl-3-hydroxy-3-(2-phenylethyl)hexanoate (II)

To a solution of diisopropylamine (32.2 ml, 230 mmol) in tetrahydrofuran (240 ml) at −58° is added 2.63 M n-butyl lithium in hexane (87.4 ml, 230 mmol) over one hour. Ethyl acetate (21.4 ml, 220 mmol) is then added and the reaction mixture stirred for 1 hour during which time the reaction mixture was cooled to −70°. 1-Phenyl-3-hexanone (I, 35.2 g, 200 mmol) is added slowly over 30 minutes and the reaction mixture stirred cold for 1 hour. The mixture was quenched with aqueous ammonium chloride (100 ml) and warmed to 20–25°. The mixture is then acidified with hydrochloric acid (4 M). The desired product is extracted into methyl t-butyl ether and dried over magnesium sulfate and concentrated to give the title compound, TLC $R_f$=0.71 (ethyl acetate/hexane, 30/70); NMR ($CDCl_3$) 7.28–7.12, 4.13, 3.60, 2.73–2.63, 2.50, 1.83–1.77, 1.58–1.53, 1.41–1.36, 1.24 and 0.93 L; CMR ($CDCl_3$) 173.0, 143.2, 128.5, 128.4, 128.3, 128.1, 125.8, 72.8, 60.6, 42.9, 41.3, 30.1, 17.0, 14.6 and 14.2 L; MS (CI, ammonia) m/z (relative intensity) 282 (100), 264 (63), 247 (10), 194 (13), 172 (5), 159 (5).

Example 2

3-Hydroxy-3-(2-phenylethyl)hexanoic Acid (III)

Ethyl-3-hydroxy-3-(2-phenylethyl)hexanoate (II, EXAMPLE 1, 200 mmol) is dissolved in methanol (423 ml) and 2M sodium hydroxide (150 ml, 300 mmol) is added. The reaction mixture is stirred at 20–25° overnight. Methanol is removed and the remaining aqueous mixture is acidified with hydrochloric acid (4 M). The desired product is extracted into methyl t-butyl ether and dried over magnesium sulfate. The product is concentrated to give the title compound, TLC $R_f$=0.10 (ethyl acetate/hexane, 30/70); NMR ($CDCl_3$) 7.43–7.13, 2.77–2.62, 2.06, 1.87–1.76, 1.63–1.57, 1.45–1.31 and 0.93 L; CMR ($CDCl_3$) 176.9, 141.9, 128.4, 128.3, 125.9, 73.4, 42.7, 41.4, 40.9, 31.9, 17.0 and 14.5 L; MS (CI, ammonia) m/z (relative intensity) 254 (100), 236 (28), 218 (3), 194 (3), 159 (5).

Example 3

R-3-Hydroxy-3-(2-phenylethyl)hexanoic Acid, (1R, 2S)-norephedrine Salt (IV)

3-Hydroxy-3-(2-phenylethyl)hexanoic acid (III, EXAMPLE 2, 2.83 g, 11.97 mmol adjusted for methyl t-butyl ether) is dissolved in acetonitrile (15 ml). (1R,2S)-Norephedrine (910 mg, 5.99 mmol 0.5 equiv.) is added and the mixture stirred overnight at 20–25°. After approximately one hour, the product began to precipitate. The following morning the slurry was cooled to 0° for 1 hour before filtering to collect the hydroxyacid salt. The cake is washed with acetonitrile (9 ml cold) and dried under reduced pressure with heat to give the desired product.

This material (ca. 1.5 g) is slurried in acetonitrile (21 ml) and heated to 70° for 30 minutes. The resulting solution is gradually cooled to 20–25° as the product precipitates. After 2 hours at 20–25°, the product is collected by vacuum filtration, washed with acetonitrile (21 ml) and dried at 20–25° under reduced pressure.

Again, this material is slurried in acetonitrile (21 ml) and heated to 70° for 30 minutes. The resulting solution is gradually cooled to room 20–25° as the product precipitates. After 2 hours at 20–25°, the product is collected by vacuum filtration, washed with acetonitrile (21 ml) and dried at 20–25° under reduced pressure to give the title compound, mp=113–117°; NMR (methanol) 7.41–7.08, 5.18, 4.98, 3.15, 2.65–2.60, 2.34, 1.79–1.73, 1.56–1.52, 1.43–1.37, 1.06 and 0.92 L; CMR (methanol) 181.4, 144.6, 142.2, 130.2–129.3, 127.6, 127.1, 74.5, 73.9, 54.0, 46.4, 43.6, 43.4, 31.9, 31.9, 18.6, 15.7 and 12.9 L; MS (CI, ammonia) m/z (relative intensity) 388 (25), 303 (15), 254 (30), 236 (7), 152 (100); $[I]^{25}_D$=16 (C=1.0, methanol).

Example 4

(6R)-5,6-Dihydro-4-hydroxy-6-[1-(2-phenyl)ethyl]-6-propyl-2H-pyran-2-one (VI)

R-3-Hydroxy-3-(2-phenylethyl)hexanoic acid, (1R,2S)-norephedrine salt (IV, EXAMPLE 3, 81 g, 209 mmol) is converted to the free acid, R-3-hydroxy-3-(2-phenylethyl) hexanoic acid by slurring the salt in ethyl acetate (810 ml) and adding hydrochloric acid (1 M, 810 ml). The free acid is extracted into the ethyl acetate and the ethyl acetate layer collected and concentrated to an oil. The free acid is then redissolved in tetrahydrofuran (490 ml) and the solution cooled to −10°. Carbonyl-diimidazole (37.3 g, 230 mmol) is added and the reaction mixture stirred cold for 2 hours. Monoethyl malonate magnesium salt (65.9 g, 230 mmol) is added and the reaction mixture gradually warmed to 20–25° while stirring overnight. The reaction is quenched with hydrochloric acid (1 M, 490 ml) and the organic layer collected. The organic layer is washed with a sodium bicarbonate solution and concentrated to 294 ml containing R-ethyl 5-hydroxy-7-phenyl-5-propylheptanoate (V). A solution of sodium hydroxide (0.5 M, 460 ml, 230 mmol) is added to the concentrated solution and the resulting cloudy mixture stirred at 20–25° overnight. Methyl t-butyl ether is added and the aqueous layer collected. The aqueous phase is acidified with hydrochloric acid (4 M) and the product is extracted into methyl t-butyl ether. The methyl t-butyl ether layer is dried over sodium sulfate and concentrated to give the title compound, TLC $R_f$=0.22 (ethyl acetate/hexane, 50/50); NMR (CDCl$_3$) 7.29–7.13, 3.39, 2.70, 2.71–2.62, 1.98–1.93, 1.74–1.66, 1.45–1.34 and 0.93 L; CMR (CDCl$_3$) 176.89, 167.5, 140.4, 128.6, 128.4, 128.2, 128.2, 126.3, 83.2, 60.1, 47.1, 44.3, 40.7, 40.4, 29.6, 16.8 and 14.5 L; MS (CI, ammonia) m/z (relative intensity) 278 (100), 254 (15), 236 (15), 217 (5), 195 (5), 159 (3).

Example 5

[3α(R),6(R)]5,6-Dihydro-4-hydroxy-3-[(Z)-1-(3-nitrophenyl)propenyl]-6-[1-(2-phenyl)ethyl]-6-propyl-2H-pyran-2-one (VII, Major Component) and [3α(R),6(R)]5,6-dihydro-4-hydroxy-3-[(E)-1-(3-nitrophenyl)propenyl]-6-[1-(2-phenyl)ethyl]-6-propyl-2H-pyran-2-one (VII, Minor Component)

(6R)-5,6-dihydro-4-hydroxy-6-[1-(2-phenyl)ethyl]-6-propyl-2H-pyran-2-one (VI, EXAMPLE 4, 50.0 g, 187 mmol) is combined with m-nitropropiophenone (33.5 g, 187.2 mmol) and 375 ml of THF. Pyridine is added (31.0 mL, 374 mmol), and the resultant mixture is stirred and cooled to below −5. A solution is prepared by adding titanium tetrachloride (31 ml, 280 mmol) to 80 ml of toluene, and this solution is added to the mixture in a controlled manner to maintain the reaction temperature below 10°. Toluene (15 ml) is used to rinse in all of the titanium tetrachloride solution and at the end of this addition, the reaction mixture is warmed to between 35–45° and maintained in this range for about 16 hours. The reaction mixture is cooled to 0° and water (200 ml) is added in a single portion. This mixture is stirred until all solids dissolve. The mixture is warmed to at least 15° and then transferred to a separatory funnel using water (250 ml) and ethyl acetate (500 ml) to dilute the mixture. The aqueous layer is separated, removed, extracted with ethyl acetate (150 ml) and discarded. The primary organic layer is washed sequentially with hydrochloric acid (1 N, 2×150 ml), water (150 ml) and saturated sodium bicarbonate (150 ml). Each wash is extracted with the ethyl acetate (150 ml) extract prior to disposal. At this point the primary organic layer and the extract are combined and concentrated under reduced pressure to give a concentrate. The concentrate is then dissolved in methylene chloride (350 ml). This solution is extracted with a total of 500 ml of 1 N sodium hydroxide (4×50 ml, then 3×100 ml). The combined aqueous extracts are washed with a total of 500 ml of methylene chloride (4×50 ml, then 3×100 ml) and then treated with hydrochloric acid (3 N, 150 ml). The acidified mixture is extracted with methylene chloride (400 ml, then 6×100 ml) and the combined organic extracts are washed with water (200 ml) and then saline (200 ml). After drying further with anhydrous sodium sulfate, the mixture is filtered through a pad of magnesol and then concentrated under reduced pressure to give the mixture of title compounds, TLC $R_f$=0.18 for (Z)-isomer, 0.28 for (E)-isomer (ethyl acetate/hexane, 1/1); CMR (CDCl$_3$) 166.93, 166.53, 148.27, 142.53, 142.39, 140.96, 132.23, 132.12, 131.82, 131.74, 129.87, 129.12, 128.55, 128.14, 126.16, 121.67, 120.56, 101.09, 81.77, 39.78, 35.23, 29.73, 16.91, 15.75, 15.69 and 14.23 L; MS (CI+NH$_3$) m/z (relative intensity) 439 (100), 422 (18), 409 (9), 392 (9), 278 (9), 194 (10), 136 (9).

Example 6

[3α(R),6(R)]5,6-dihydro-4-hydroxy-3-[1-(3-nitrophenyl)propyl]-6-[1-(2-phenyl)ethyl]-6-propyl-2H-pyran-2-one (VII)

[3α(R),6(R)]5,6-Dihydro-4-hydroxy-3-[(Z)-1-(3-nitrophenyl)propenyl]-6-[1-(2-phenyl)ethyl]-6-propyl-2H-pyran-2-one (VII, EXAMPLE 5, 4.24 g, 10 mmol) and [(1,5-cyclooctadiene)rhodium(I)-1,2-bis-(2R,5R)-dimethyl-phospholano)benzene]-tetrafluoroborate (6.0 mg, 0.01 mmol) are combined in an inert atmosphere and dissolved in 20 ml of deoxygenated methanol. The atmosphere is replaced with hydrogen at a pressure of 80 psig or more and the reaction is warmed to 55° and stirred for 24 hours. At the end of this period, the reaction is cooled to 20–25° and the hydrogen is replaced with an inert atmosphere. The reaction mixture is concentrated under reduced pressure and the residue is crystallized from a methanol/water mixture (3/1) to give the title compound, TLC $R_f$=0.49 (ethyl acetate/ hexanes, 1/1); HPLC rt=6.93 min; NMR (CDCl$_3$/CD$_3$OD, 1/1) 8.08, 7.80, 7.56, 7.22, 7.07–6.88, 3.98, 3.33–3.30, 2.50–2.37, 1.92–1.70, 1.58–1.50, 1.22–1.14, 0.76 and 0.72 L; CMR (CDCl$_3$/CD$_3$OD, 1/1) 169.05, 166.66, 148.66, 147.79, 141.99, 135.30, 129.21, 129.02, 128.70, 126.55, 123.51, 121.23, 105.13, 81.39, 42.58, 40.39, 40.09, 36.76, 30.38, 24.95, 17.44, 14.54 and 13.04 L.

Example 7

[3α(R),6(R)]3-[1-(3-Aminophenyl)propyl]-5,6-dihydro-4-hydroxy-6-[1-(2-phenyl)ethyl]-6-propyl-2H-pyran-2-one (IX)

To a solution of [3α(R),6(R)]5,6-dihydro-4-hydroxy-3-[1-(3-nitrophenyl)propyl]-6-[1-(2-phenyl)ethyl]-6-propyl-2H-pyran-2-one (VIII, EXAMPLE 6, 0.6993 g, 1.651 mmol) in THF (50 ml) is added palladium on carbon (5%, 50% water wet, 0.2574 g, 0.06048 mmol, 0.0366 equiv) and the mixture hydrogenated at 50 psi on a Parr shaker for 21 hrs. Celite (2.07 g) is added and the catalyst removed by vacuum filtration and rinsed with THF. The filtrate is concentrated to give the title compound, TLC $R_f$=0.45 (ethyl acetate/hexanes, 1/1); HPLC rt=5.18 min.

Example 8

[R-(R*,R*)]-N-[3-[1-[5,6-dihydro-4-hydroxy-2-oxo-6-(2-phenylethyl)-6-propyl-2H-pyran-3-yl]propyl] phenyl]-5-(trifluoromethyl)-2-pyridinesulfonamide (X)

To a mixture of [3α(R),6(R)]3-[1-(3-aminophenyl) propyl]-5,6-dihydro-4-hydroxy-6-[1-(2-phenyl)ethyl]-6-propyl-2H-pyran-2-one (IX, EXAMPLE 7, crude 0.555 g, 1.378 mmol based on title compounds XIX), in methylene chloride (3.10 ml), DMSO (0.100 ml, 1.409 mmol, 1.02 equiv) and pyridine (0.56 ml, 6.92 mmol, 5.02 equiv) is added the crude mixture of 5-(trifluoromethyl)-2-pyridinesulfonyl chloride in methylene chloride prepared above (5.23 ml, ~2.3 mmol based on thiol, ~1.7 equiv) at −25 to −30° over 2 hours, titrating with the 5-(trifluoromethyl)-2-pyridinesulfonyl chloride mixture to an HPLC endpoint of 1.4 area % residual [3α(R),6(R)]3-[1-(3-aminophenyl)propyl]-5,6-dihydro-4-hydroxy-6-[1-(2-phenyl)ethyl]-6-propyl-2H-pyran-2-one. Aqueous hydrochloric acid (1 M, 6.2 ml, 6.2 mmol, 4.50 equiv) and ethyl acetate (5.2 ml) is added and the phases separated. The aqueous phase is washed with methylene chloride (10 ml) and the combined organic phases dried on magnesium sulfate and concentrated. This concentrate is loaded on a silica gel column (9.76 g silica gel) packed with ethyl acetate/hexanes (10/90) and the product eluted with the following ethyl acetate in hexanes mixtures (50 ml 10%, 100 ml 20%, 100 ml 30%, and 50 ml 40%). The eluent is combined and concentrated to an oil with an ethyl acetate chase. Ethyl acetate is added (5.2 ml) and the product precipitated by slow addition of heptane (15 ml). The resultant slurry is cooled to −30° and the precipitate collected by vacuum filtration, washed with a −30° mixture of ethyl acetate (1 ml) and heptane (4 ml) and dried in a nitrogen stream to give the title compound, mp=86–89/; TLC $R_f$=0.66 (ethyl acetate/hexane, 50/50); NMR (CD$_3$OD) 8.94, 8.19, 8.02, 7.25–6.97, 3.93, 2.68–2.52, 2.15–2.09, 1.96–1.64, 1.33, 0.88 and 0.83 L; CMR (CD$_3$OD) 169.9, 167.0, 161.6, 148.1, 147.6, 142.8, 137.7, 137.0, 130.1, 129.5, 129.3, 127.0, 126.1, 124.2, 122.6, 120.3, 106.2, 81.9, 43.6, 40.5, 40.5, 37.4, 30.9, 25.8, 17.9, 14.7 and 13.3 L; MS (CI, ammonia) m/z (relative intensity) 621 (1.7), 620 (5.4), 604 (1.1), 603 (3.4), 411 (12), 394 (12), 148 (100); IR (mull) 1596, 1413, 1359, 1326, 1177, 1149, 1074 and 720 cm$^{-1}$ (same solid state form as reference).

Example 9

[3α(R),6(R)]5,6-Dihydro-4-hydroxy-3-[1-(3-nitrophenyl)propyl]-6-[1-(2-phenyl)ethyl]-6-propyl-2H-pyran-2-one (VIII)

[3α(R),6(R)]5,6-Dihydro-4-hydroxy-3-[(Z)-1-(3-nitrophenyl)propenyl]-6-[1-(2-phenyl)ethyl]-6-propyl-2H-pyran-2-one (VII, EXAMPLE 5, 1.0 g, 2.37 mmol) and sodium carbonate (0.025 g, 0.23 mmol) are placed in a 50 ml Parr pressure vessel which is then purged with hydrogen (by pressurization and venting four times with 70 psi hydrogen). To this mixture is added degassed methanol (4.5 ml), which was degassed by nitrogen bubbling for 2 to 3 hr with stirring at 20–25°. The vessel is again Purged with hydrogen (by pressurization and venting two times with 70 psi hydrogen). The reactor is charged to 70 psi hydrogen and heated to an internal temperature of about 50° (resulting in an internal pressure of abut 80 psi). Upon reaching the required temperature, the vessel is de-pressurized and a mixture of [(1,5-cyclooctadiene)rhodium(I)-1,2-bis-(2R,5R)-dimethylphospholano)benzene]tetrafluoroborate (1.4 mg, 2.3 mmol) in degassed methanol (0.5 ml) is added. The vessel is then re-pressurized to 80 psi and heated at 55–60°. After stirring for 22 hr. the vessel is vented into a fume hood. After transfer to a round bottom flask, the solvent is remove under reduced pressure. The residue is partitioned between methylene chloride (10 ml) and hydrochloric acid (2 M, 10 ml). The organic phase is separated, washed with saline (10 ml), dried over magnesium sulfate, filtered and concentrated under reduced pressure to give the title compound. The product is analyzed by NMR (200 Mhz, CD$_3$OD) and by chiral Super Critical Fluid Chromatography 20 min retention time.

Example 10

[3α(R),6(R)]5,6-dihydro-4-hydroxy-3-[1-(3-nitrophenyl)propyl]-6-[1-(2-phenyl)ethyl]-6-propyl-2H-pyran-2-one (VIII)

Following the general procedure of EXAMPLE 9 and making non-critical variations, but performing the reaction at 20–25°, at 200 psi, with a catalyst loading (mol %) of 0.1 and using no base, the title compound is not observed in 2 hr and is obtained in 5% in 48 hr.

Example 11

[3α(R),6(R)]5,6-dihydro-4-hydroxy-3-[1-(3-nitrophenyl)propyl]-6-[1-(2-phenyl)ethyl]-6-propyl-2H-pyran-2-one (VIII)

Following the general procedure of EXAMPLE 9 and making non-critical variations, but performing the reaction at 20–25°, at 200 psi, with a catalyst loading (mol %) of 0.1 and using sodium methoxide (1 equivalent), the title compound is observed in trace amounts in 2 hr; in 35% in 21 hr and in 100% in 96 hr with an enantiomeric purity of 88.7%.

Example 12

[3α(R),6(R)]5,6-dihydro-4-hydroxy-3-[1-(3-nitrophenyl)propyl]-6-[1-(2-phenyl)ethyl]-6-propyl-2H-pyran-2-one (VIII)

Following the general procedure of EXAMPLE 9 and making non-critical variations, but performing the reaction at 20–25°, at 200 psi, with a catalyst loading (mol %) of 0.1 and using sodium methoxide (0.1 equivalent), the title compound is observed in trace amounts in 2 hr; in 60% in 24 hr and in 100% in 96 hr with an enantiomeric purity of 94.3%.

CHART A

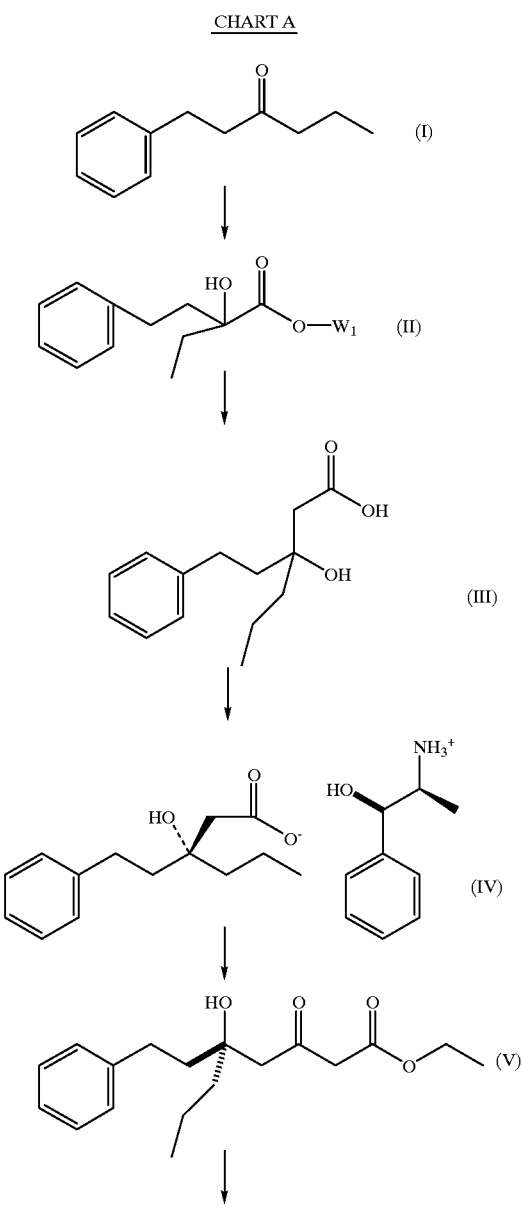

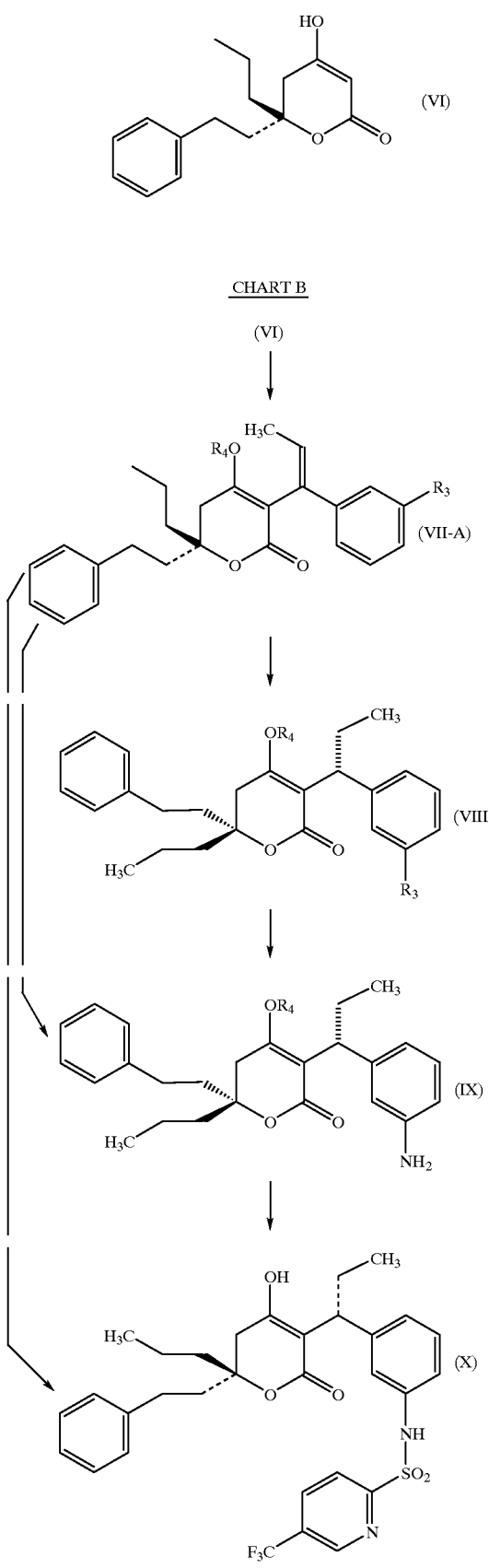
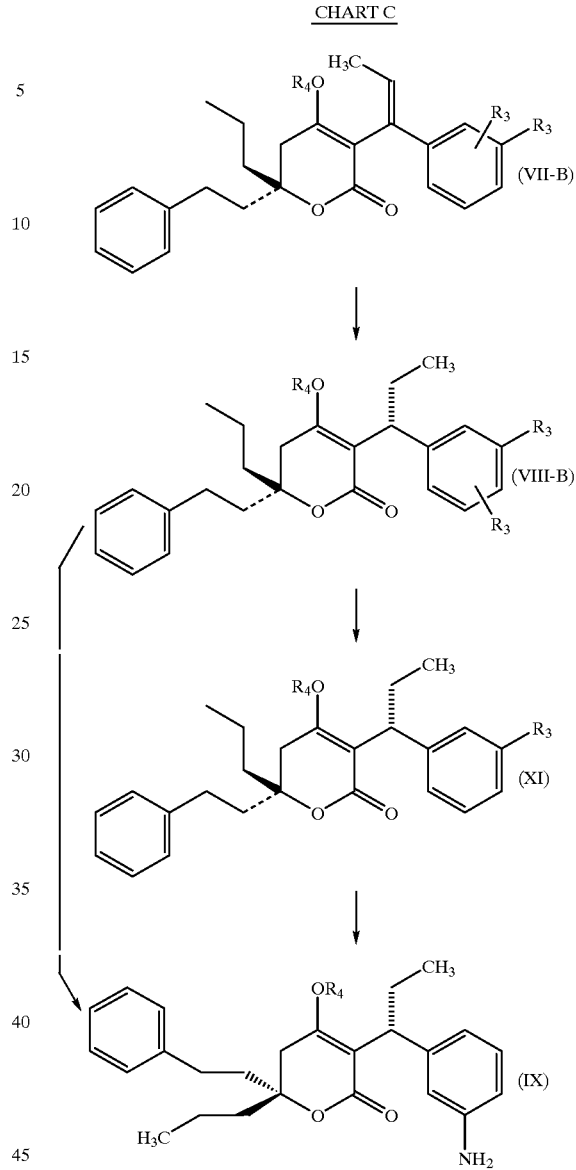
What is claimed is:
1. A process for the preparation of a compound of the formula:
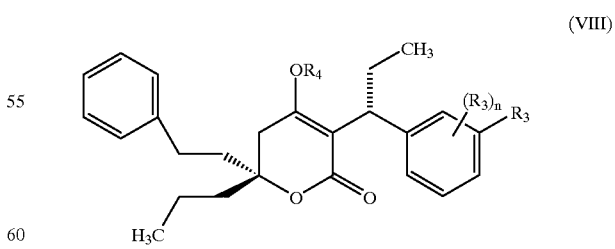
where $R_3$ is selected from the group consisting of:
—$NO_2$,
—$NH_2$,
—NH—$SO_2$-[4-trifluoromethylpyridin-2-yl],
—N(—$CH_2$-φ)$_2$, —N($R_{3-1}$)($R_{3-2}$) where $R_{3-1}$ and $R_{3-2}$ are the same or different and are:
—H,
—CO—O—(t-butyl),
—CO—O—$CH_2$-φ,
—CO—$CH_3$,
—CO-φ,
—Cl,
—Br,
—I,
—OH,
—O—$SO_2$—$CF_3$, where n is 0 or 1 with the provisos, (1) that when n is 0 the $R_3$ group must be in the meta position and (2) that when n is 1, one of $R_3$ must be —Cl, —Br, —I, —OH or —O—$SO_2$—$CF_3$, where $R_4$ is selected from the group consisting of —H and —Si($CH_3$)$_3$, which comprises hydrogenating a compound of the formula:

(VII)

the E-geometrical isomer thereof or a mixture of the Z- and E-isomers, where $R_3$ and $R_4$ are as defined above, in the presence of catalyst containing Rh, a chiral ligand with at least one phosphorous atom where the hydrogenation is conducted in the presence of a base.

2. A process according to claim 1 where the catalyst is the (2R,5R)-enantiomer of a catalyst of the formula:

$X_1$—$Rh^+$-cyclooctadiene $X_2^-$ where $X_1$ is selected from the group consisting of:
(1) BPE

BPE where $X_{1-1}$ is —$CH_3$ or —$C_2H_5$,
(2) DuPHOS

DuPHOS where $X_{1-1}$ is as defined above;
where $X_2$ is selected from the group consisting of:

(1) $BF_4^-$ and
(2) $CF_3$—CO—$O^-$.

3. A process according to claim 1 where a mixture of E/Z-isomers of (VII) is used.

4. A process according to claim 1 where n is 0.

5. A process according to claim 1 where $R_3$ is —$NO_2$, —$NH_2$ and —N($R_{3-1}$)($R_{3-2}$) where one of $R_{3-1}$ and $R_{3-2}$ is —H and the other is —CO—O—(t-butyl).

6. A process according to claim 5 where $R_3$ is —$NO_2$.

7. A process according to claim 1 where $R_4$ is —H.

8. A process according to claim 1 where the base has a $pK_a$>5.

9. A process according to claim 1 where the base is selected from the group consisting of hydroxide, alkoxide where the alkyl group is from $C_1$–$C_5$ bicarbonate, carbonate, di- and tribasic phosphate, borate, fluoride and $R_aR_bR_cN$ where $R_a$, $R_b$ and $R_c$ are the same or different and are:
H—,
$C_1$–$C_4$ alkyl,
φ-,
$R_dR_eR_fSi$— where the $R_d$, $R_e$ and $R_f$ are the same or different and are $C_1$–$C_3$ alkyl with the proviso that not more than one of the $R_a$, $R_b$ and $R_c$ are H—.

10. A process according to claim 9 where the base is selected from the group consisting of hydroxide, methoxide, ethoxide, t-butoxide, t-amylate, s-butoxide, di- and tribasic phosphate and carbonate.

11. A process according to claim 9 where the base is methoxide or carbonate.

12. A process according to claim 1 where the base is present in an amount of less than one equivalent.

13. A process according to claim 12 where the base is present in an amount of about 0.1 equivalents.

14. A process according to claim 1 where the catalyst is of formula (2) DuPHOS.

15. A process according to claim 1 where $X_2$ is $BF_4^-$.

16. A process according to claim 1 where $X_{1-1}$ is —$CH_3$.

17. A process according to claim 1 where the ratio (in moles) of substrate/catalyst is from about 200/1 to 5,000/1.

18. A process according to claim 17 where the ratio (in moles) of substrate/catalyst is from about 500/1 to 3,000/1.

19. A process according to claim 18 where the ratio (in moles) of substrate/catalyst is from about 1,000/1 to 2,000/1.

20. A process according to claim 1 where the temperature at which the hydrogenation is performed is from about 20° to about 120°.

21. A process according to claim 20 where the temperature at which the hydrogenation is performed is from about 40° to about 80°.

22. A process according to claim 21 where the temperature at which the hydrogenation is performed is from about 50° to about 65°.

23. A process according to claim 1 where the pressure is from about 40 to about 1,000 psi.

24. A process according to claim 23 where the pressure is from about 70 to about 500 psi.

25. A process according to claim 24 where the pressure is from about 70 to about 90 psi.

26. A process according to claim 1 where the catalyst is added after the compound of formula (VII), base, solvent and hydrogen are contacted.

27. A process according to claim 26 where the catalyst is added after the compound of formula (VII), base, solvent and hydrogen are contacted and the reaction temperature is reached.

28. A process according to claim 23 where the compound (VIII) is [3α(R),6(R)]5,6-dihydro-4-hydroxy-3-[1-(3-nitrophenyl)propyl]-6-[1-(2-phenyl)ethyl]-6-propyl-2H-pyran-2-one.

29. A process for the preparation of a compound of the formula:

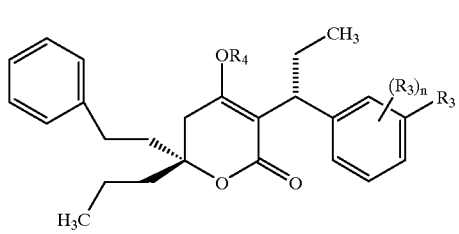

(VIII)

where $R_3$ is selected from the group consisting of:
—$NO_2$,
—$NH_2$,
—NH—$SO_2$-[4-trifluoromethylpyridin-2-yl],
—N(—$CH_2$-φ)$_2$,
—N($R_{3-1}$)($R_{3-2}$) where $R_{3-1}$ and $R_{3-2}$ are the same or different and are:
—H,
—CO—O—(t-butyl),
—CO—O—$CH_2$-φ,
—CO—$CH_3$,
—CO-φ,
—Cl
—Br,
—I,
—OH,
—O—$SO_2$—$CF_3$;

where n is 0 or 1 with the provisos (1) that when n is 0 the $R_3$ group must be in the meta position and (2) that when n is 1, one of $R_3$ must be —Cl, —Br, —I, —OH or —O—$SO_2$—$CF_3$;

where $R_4$ is selected from the group consisting of $Na^+$, $K^+$, $Li^+$, $Cs^+$ and $(R_{4-1})_4N^+$ where $R_{4-1}$ are the same or different and are $CH_3$—, $C_2H_5$—, $C_4H_9$—, φ-$CH_2$— and $C_8H_{17}$— which comprises hydrogenating a compound of the formula:

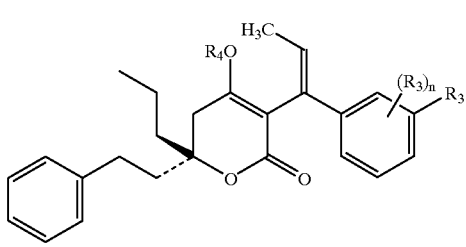

(VII)

the E-geometrical isomer thereof or a mixture of the Z- and E-isomers, where $R_3$ and $R_4$ are as defined above, in the presence of catalyst containing Rh, a chiral ligand with at least one phosphorous atom.

30. A process according to claim 29 where the catalyst is the (2R,5R)-enantiomer of a catalyst of the formula:

$X_1$—$Rh^+$-cyclooctadiene $X_2^-$ where $X_1$ is selected from the group consisting of:

(1) BPE

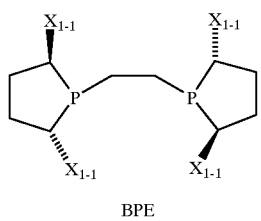

BPE where $X_{1-1}$ is —$CH_3$ or —$C_2H_5$, (2) DuPHOS

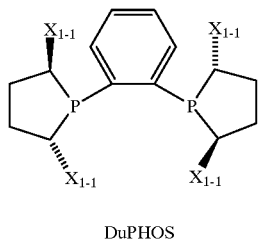

DuPHOS where $X_{1-1}$ is as defined above;

where $X_2$ is selected from the group consisting of:
(1) $BF_4^-$ and
(2) $CF_3$—CO—$O^-$.

31. A process according to claim 29 where a mixture of E/Z-isomers of (VII) is used.

32. A process according to claim 29 where n is 0.

33. A process according to claim 29 where $R_3$ is —$NO_2$, —$NH_2$ and —N($R_{3-1}$)($R_{3-2}$) where one of $R_{3-1}$ and $R_{3-2}$ is —H and the other is —CO—O—(t-butyl).

34. A process according to claim 33 where $R_3$ is —$NO_2$.

35. A process according to claim 29 where $R_4$ is $Na^+$, $K^+$, $Li^+$, $Cs^+$ and $(R_{4-1})_4N^+$.

36. A process according to claim 29 where the catalyst is of formula (2) DuPHOS.

37. A process according to claim 29 where $X_2$ is $BF_4^-$.

38. A process according to claim 29 where $X_{1-1}$ is —$CH_3$.

39. A process according to claim 29 where the ratio (in moles) of substrate/catalyst is from about 200/1 to 5,000/1.

40. A process according to claim 39 where the ratio (in moles) of substrate/catalyst is from about 500/1 to 3,000/1.

41. A process according to claim 40 where the ratio (in moles) of substrate/catalyst is from about 1,000/1 to 2,000/1.

42. A process according to claim 29 where the temperature at which the hydrogenation is performed is from about 20° to about 120°.

43. A process according to claim 42 where the temperature at which the hydrogenation is performed is from about 40° to about 80°.

44. A process according to claim 43 where the temperature at which the hydrogenation is performed is from about 50° to about 65°.

45. A process according to claim 29 where the pressure is from about 40 to about 1,000 psi.

46. A process according to claim 45 where the pressure is from about 70 to about 500 psi.

47. A process according to claim 46 where the pressure is from about 70 to about 90 psi.

48. A process according to claim 29 where the catalyst is added after the compound of formula (VII), base, solvent and hydrogen are contacted.

49. A process according to claim 48 where the catalyst is added after the compound of formula (VII), base, solvent and hydrogen are contacted and the reaction temperature is reached.

50. A process according to claim 29 where the compound (VIII) is [3α(R),6(R)]5,6-dihydro-4-hydroxy-3-[1-(3-nitrophenyl)propyl]-6-[1-(2-phenyl)ethyl]-6-propyl-2H-pyran-2-one.

* * * * *